US010799124B2

(12) United States Patent
Raglund et al.

(10) Patent No.: US 10,799,124 B2
(45) Date of Patent: Oct. 13, 2020

(54) DATA TRANSFER OF A HEART RATE AND ACTIVITY MONITOR ARRANGEMENT AND A METHOD FOR THE SAME

(71) Applicants: Jari Raglund, Helsinki (FI); Vesa Saynajakangas, Espoo (FI); Tommi Opas, Espoo (FI)

(72) Inventors: Jari Raglund, Helsinki (FI); Vesa Saynajakangas, Espoo (FI)

(*) Notice: Subject to any disclaimer, the term of this patent is extended or adjusted under 35 U.S.C. 154(b) by 374 days.

(21) Appl. No.: 14/787,950

(22) PCT Filed: Apr. 28, 2014

(86) PCT No.: PCT/FI2014/050308
§ 371 (c)(1),
(2) Date: Oct. 29, 2015

(87) PCT Pub. No.: WO2014/177764
PCT Pub. Date: Nov. 6, 2014

(65) Prior Publication Data
US 2016/0073904 A1  Mar. 17, 2016

(30) Foreign Application Priority Data

Apr. 30, 2013 (GB) .................................. 1307743.3

(51) Int. Cl.
A61B 5/02 (2006.01)
A61B 5/0205 (2006.01)
(Continued)

(52) U.S. Cl.
CPC .......... A61B 5/0205 (2013.01); A61B 5/0022 (2013.01); A61B 5/0024 (2013.01);
(Continued)

(58) Field of Classification Search
CPC ... A61B 5/0205; A61B 5/7282; A61B 5/0022; A61B 5/0024; A61B 5/1118;
(Continued)

(56) References Cited

U.S. PATENT DOCUMENTS 5,827,180 A * 10/1998 Goodman ............ A61B 5/0002
600/300
2003/0065257 A1 * 4/2003 Mault ................ A61B 5/02055
600/407
(Continued)

FOREIGN PATENT DOCUMENTS

EP 2025368 A2 2/2009
EP 2239023 A1 10/2010
(Continued)

OTHER PUBLICATIONS

International Search Report, dated Aug. 7, 2014, from corresponding PCT application.
(Continued)

Primary Examiner — Navin Natnithithadha
Assistant Examiner — Andrey Shostak
(74) Attorney, Agent, or Firm — Nixon & Vanderhye

(57) ABSTRACT

The invention relates generally to data transfer of the heart rate and activity monitor arrangement. The arrangement includes heart rate monitoring elements for monitoring a user's heart rate, motion detection elements for monitoring the user's activity, control elements for obtaining data from the heart rate monitoring elements and from the motion detection elements, and a transferring element including at least one transceiver. Further, the transferring element is arranged to transfer heart rate and/or activity data monitored by the heart rate and activity monitor arrangement to an external entity directly via a wireless cellular communications system.

13 Claims, 2 Drawing Sheets

(51) Int. Cl.
*A61B 5/11* (2006.01)
*G06F 19/00* (2018.01)
*A61B 5/00* (2006.01)
*A61B 5/0245* (2006.01)

(52) U.S. Cl.
CPC .......... *A61B 5/1118* (2013.01); *A61B 5/7282* (2013.01); *G06F 19/3418* (2013.01); *A61B 5/0245* (2013.01); *A61B 2503/10* (2013.01); *A61B 2560/0475* (2013.01); *A61B 2562/0219* (2013.01)

(58) Field of Classification Search
CPC .............. A61B 5/0245; A61B 2503/10; A61B 2560/0475; A61B 2562/0219; G06F 19/3418
See application file for complete search history.

(56) References Cited

U.S. PATENT DOCUMENTS

| | | | |
|---|---|---|---|
| 2007/0197878 A1* | 8/2007 | Shklarski | A61B 5/02055 600/300 |
| 2007/0276200 A1* | 11/2007 | Ahola | A61B 5/02438 600/300 |
| 2009/0047645 A1* | 2/2009 | Dibenedetto | H04M 1/72563 434/258 |
| 2009/0058637 A1* | 3/2009 | Kuo | A61B 5/0002 340/539.12 |
| 2010/0292050 A1 | 11/2010 | Dibenedetto et al. | |
| 2011/0224511 A1 | 9/2011 | Saynajakangas et al. | |
| 2011/0251753 A1* | 10/2011 | Saito | B60L 11/1816 701/31.4 |
| 2012/0083705 A1 | 4/2012 | Yuen et al. | |
| 2012/0101350 A1 | 4/2012 | Bychkov | |
| 2012/0221254 A1 | 8/2012 | Kateraas et al. | |
| 2014/0073486 A1 | 3/2014 | Ahmed et al. | |

FOREIGN PATENT DOCUMENTS

| | | | | |
|---|---|---|---|---|
| EP | 2320317 A1 | 5/2011 | | |
| EP | 2 335 563 A1 | 6/2011 | | |
| EP | 2407218 A2 | 1/2012 | | |
| WO | 2006/021956 A2 | 3/2006 | | |
| WO | 2007147083 A2 | 12/2007 | | |
| WO | 2008097524 A2 | 8/2008 | | |
| WO | 2011105914 A1 | 9/2011 | | |
| WO | 2012/061438 A2 | 5/2012 | | |
| WO | WO 2012061438 A2 * | 5/2012 | ............. | A61B 5/681 |
| WO | 2012/112407 A1 | 8/2012 | | |
| WO | 2012135325 A2 | 10/2012 | | |
| WO | 2012/172273 A1 | 12/2012 | | |

OTHER PUBLICATIONS

GB Search Report, dated Oct. 30, 2013, from corresponding GB application.
Supplementary European Search Report EP14791460 dated Dec. 15, 2016.

* cited by examiner

DATA TRANSFER OF A HEART RATE AND ACTIVITY MONITOR ARRANGEMENT AND A METHOD FOR THE SAME

TECHNICAL FIELD

Generally, the invention relates to a heart rate and activity monitor arrangement. Especially, the invention relates to data transfer of the heart rate and activity monitor arrangement and a method for the same.

BACKGROUND TECHNOLOGY

Currently, several different types of devices are on market for monitoring user's activity, heart rate and consumed calories as well as for counting steps and tracking exercises. Many of these devices, such as heart rate monitors, comprise a chest strap with means for detecting heart beats of the user. In general, this is advantageous, because heart rate monitoring gives very accurate data about user's current physical fitness and the intensity of an exercise, for example.

Unfortunately, many heart rate monitors or activity monitors suffer from data transfer problem. Prior art knows a solution, wherein a user have to carry e.g. mobile phone or some other device in addition to the heart rate monitor in order to transfer the monitored data from the device for further purposes. This can be very inconvenient, because it is difficult to carry extra devices when exercising.

Some of the heart rate monitors and/or activity monitors may have a transceiver within, but transferring data simultaneously with heart rate monitoring may cause disturbances in monitored data.

SUMMARY OF THE INVENTION

It is an object of the present invention to implement such a solution, that previously mentioned drawbacks of the prior art could be diminished. In particular, the invention is implied to solve how to transfer data between a heart rate and activity monitor arrangement and an external entity.

The objective of the invention is met by the features disclosed in the independent patent claims.

According to an embodiment of the invention, the heart rate and activity monitor arrangement comprises heart rate monitoring means for monitoring a user's heart rate, motion detection means for monitoring said user's activity, control means for obtaining data from said heart rate monitoring means and from said motion detection means, and transferring means comprising at least one transceiver. Further, said transferring means is arranged to transfer heart rate and/or activity data monitored by said heart rate and activity monitor arrangement to an external entity.

In another embodiment, the transferring means of the heart rate and activity monitor arrangement according to the present invention further comprises a GSM module or an corresponding module for connecting to wireless, cellular communications network. GSM module may be advantageous, because it enables data transfer via GSM network, which is reliable network having a wide area coverage. GSM network can also be utilized to location tracking, which may enable tracking without GPS module.

In one embodiment, the transferring means is arranged to continuously transfer data as long as a use's heart rate and/or activity monitoring device is in its activated state. This feature may enable the implementation of a portable device comprising the monitoring means of the present invention with a small-capacity memory or even without a data memory.

In another embodiment, the monitored data is stored by storing means before transferring it. This feature can be useful, because in that case data can be transferred, when it is most suitable to be performed. In an embodiment, data is transferred, after a predetermined time period has elapsed, and in another embodiment, when charging of the device is started. Transferring data same time with charging can be advantageous, because in that way data transfer does not cause any disturbance to the heart rate monitoring.

Yet, in one embodiment, the heart rate monitoring is paused, if in process, for the duration of data transfer, and in another embodiment, a heart rate profile is generated from said activity data for the duration of paused monitoring. When using a personal correlation for converting activity data to a heart rate profile, it may be possible to transfer data and still obtain both heart rate and activity data during that time period.

According to an embodiment of the invention, a method for transferring data between a heart rate and activity monitor arrangement according to the present invention and an external entity comprises steps of detecting a predetermined condition, and transferring data, when said predetermined condition is fulfilled.

In one embodiment, the method further comprises a step of pausing said heart rate monitoring, if in process, for the duration of data transfer, and in another embodiment, the method comprises a further step of generating a heart rate profile from said activity data for the duration of paused monitoring.

Some preferable embodiments of the invention are described in the dependent claims.

Significant advantages can be achieved with the present invention when compared to the prior art solution. Data transfer can be performed when it is most suitable to perform, such as during charging, when the device cannot anyway be used for heart rate and activity monitoring.

When transferring data during an exercise, the heart rate monitoring can be paused during that time. This may enable regular data transfer, and may enable using of a smaller memory in the device. Further, the heart rate profile during the time period, when it has been paused, can be generated from the activity data.

In the present document, the term "heart rate" refers the number of heartbeats per minute, which can be monitored in many ways, such as measuring the heart's electrical activity or measuring pressure waves, i.e. pulse, generated by the heart.

In the present document, the term "activity data" refers to various physical quantities, such as velocity, average velocity, maximum velocity distance, altitude variation, number of steps, step rate, type of exercise, location information, route tracking.

In the present document, the term "external entity" refers to an electronic device or a group of devices capable of obtaining data, such as a cloud. In practice, the external entity can be for example, but not limited to, terminal devices, such as a personal computer, a smart phone, a PDA, a tablet, or a server, group of servers, for example.

SHORT DESCRIPTION OF THE DRAWINGS

Next, the invention is described in more detail with reference to the appended drawings, in which FIG. 1 illustrates the concept of an embodiment of the present invention;

DETAILED DESCRIPTION OF THE EMBODIMENTS

Figure 1:
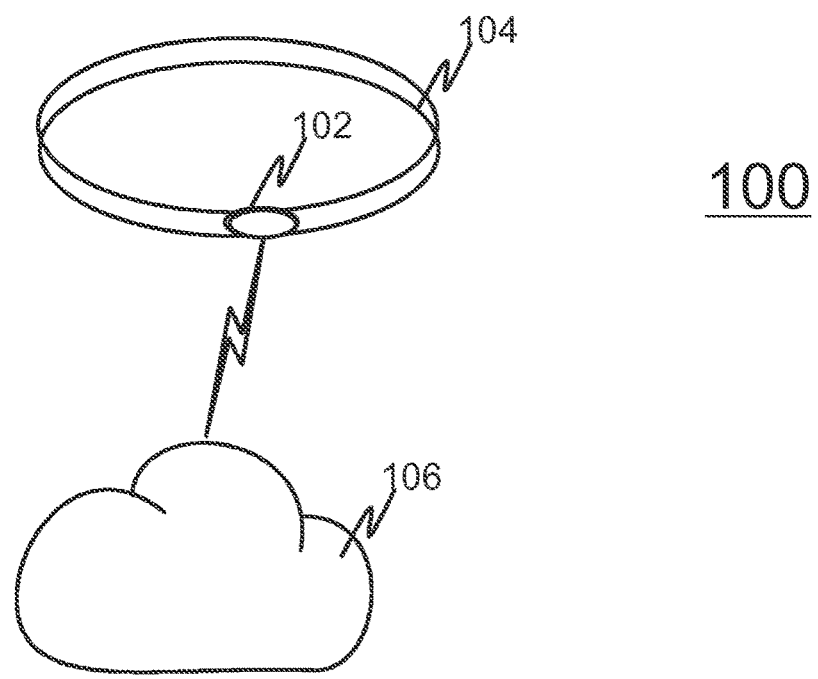
Figure 2:
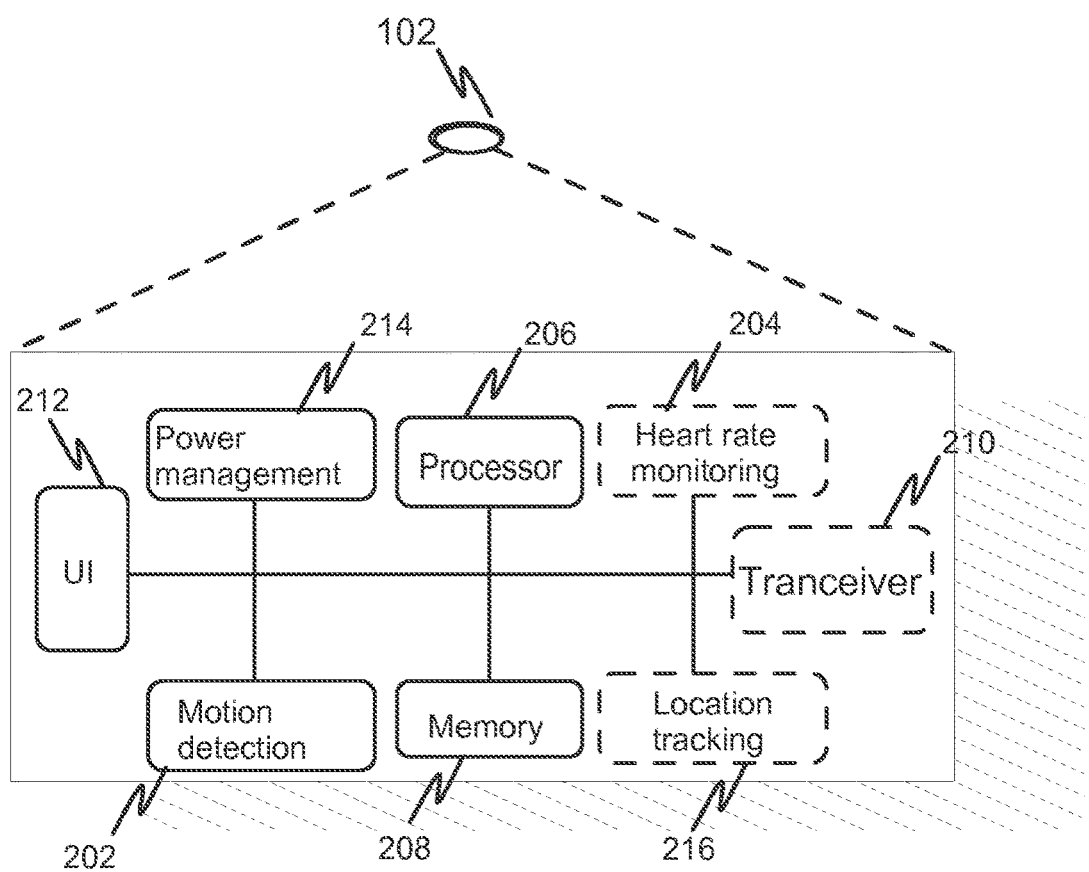
FIG. 2 illustrates the internals of an embodiment of a portable device in accordance of the present invention.

FIG. 1 illustrates the concept of an embodiment of the present invention and FIG. 2 the internals of an embodiment of a portable device in accordance of the present invention. In one embodiment, the heart rate and activity monitor arrangement 100 comprises heart rate monitoring means for monitoring a user's heart rate, motion detection means for monitoring said user's activity, control means for obtaining data from said heart rate monitoring means and/or from said motion detection means, transferring means comprising at least one transceiver capable of sending and receiving data, wherein said transferring means is arranged to transfer heart rate and/or activity data monitored by said heart rate and activity monitor arrangement to an external entity.

In one embodiment, the motion detection means 202 and the controlling means is preferably combined in a single entity, e.g. a portable device 102, which is attached to a user and/or is carried by the user. In another embodiment, part of the heart rate monitoring means 204 is also located in the portable device 102.

In one embodiment, the heart rate monitoring means comprises a chest strap 104, which is wound around the user's chest, when user's heart rate is desired to be monitored. In one embodiment, the chest strap 104 comprises electrodes (not shown) for producing heart rate data by measuring the difference in potential between the electrodes.

In one embodiment, the chest strap 104 comprises connectors (not shown) for the portable device 102 to be connected. The connectors are advantageously secure and easy to use, such as snap fastener connectors, which ensure a good connection between the device 102 and the chest strap 104. In one embodiment, the control means is configured to obtain the heart rate data measured by electrodes in the chest strap via the connectors. It is obvious for the skilled person that the chest strap can also comprise additional and/or alternative data transferring means, such as BLUETOOTH or another RF transceiver method, for example.

It is obvious to the skilled person that the heart rate can be measured by some other means than using the chest strap. However, it is advantageous that in every embodiment using other means to measure the heart rate, the portable device is configured to obtain the heart rate data.

Depending on embodiment, the chest strap and/or the control means can comprise means for processing the signal measured by the electrodes, e.g. filtering, amplifying and/or averaging it.

The portable device 102 according to the present invention further comprises motion detection means 202 for monitoring the user's activity. In one embodiment, the motion detection means comprises at least one 3D accelerometer. In one embodiment, in addition to and/or instead of the 3D accelerometer, the motion detection means comprises some other means for detecting user's motions, such as one or more gyroscopes. Preferably, the motion detection means is fastened to the portable device so that it can freely detect the movements of the portable device.

The activity data provided by the motion detection means is further obtained and stored by the control means. Preferably, the sample rate is about 10-20 sample/seconds, which provides sufficient information about the movements of the portable device. As described above, the control means can comprise means for processing the data measured by the motion detection means, e.g. filtering, amplifying and/or averaging it.

In one embodiment, the arrangement is arranged to learn a correlation between said user's heart rate and activity based on heart rate data and activity data monitored at the same time. In another embodiment, the heart rate and activity monitor arrangement according to the present invention is arranged to provide a user's heart rate profile based on the activity data by using the correlation of said user. This feature enables the user to carry the portable device and monitor only activity, whereas the heart rate profile can be converted from the activity data.

The controlling means comprises at least means, such as a processor 206, for obtaining heart rate and activity data, and data transfer means, e.g. transceiver 210, for transferring data from the device 102 and receiving upcoming data. In one embodiment, the control means further comprises storage means, such as a memory 208, for storing the obtained data. Typically, the control means also comprises user interface (UI) 212 and power management means 214. Furthermore, in some embodiments, the controlling means comprises location tracking means 216 for tracking the location of the motion detection means.

In embodiment, wherein the controlling means comprises the storage means, the storage means can be arranged in many ways. In one embodiment, the storage means comprises MMC (multimedia) card and/or micro SD card. These kinds of memory cards are well known technique, so they are not described more detailed in the present document. Requirements for the memory module are that it is fast enough and has sufficient size of memory.

Preferably, the control means comprises a user interface 212, which can comprise e.g. one or more push-buttons and/or visible and/or audible signaling means, such as one or more LED devices and/or one or more beepers. The push-buttons may have different functions, such as, but not limited to, activating device, selecting activity type, selecting heart rate and/or activity data monitoring mode. More than one function can be related to one push-button by alternating a way of pressing the button, i.e. short press vs. long press and/or a number of presses. Respectively, visible and/or audible signaling means can have different functions, such as, but not limited to, indicating the activation of the device, selected activity type, charge level of batteries, heart rate and/or activity level, etc. It is obvious to the skilled person that the visible and/or audible signaling means can also be arranged to indicate several types of malfunction situations. Respectively, more than one indication can be related to one visible/audible signaling means, such as constant light/sound vs. blinking light/sound, for example.

In addition, the control unit comprises power management means 214 comprising power means, such as batteries, for providing power for components in the portable device. Preferably, used power means are rechargeable, but it is possible to use disposable batteries.

In embodiments, wherein power means comprises rechargeable batteries, the batteries are preferably charged from mains. In an embodiment, the arrangement according to the present invention comprises a cradle for charging, which cradle is preferably formed so that the charging process can be performed by placing the portable device in the cradle. Preferably, the cradle comprises means to secure the portable device in right position in the cradle, such as magnets for securing the portable device and/or design for assisting to set the device in right position and keep it in place during charging.

In an embodiment, the cradle is connectible to mains, e.g. 240 V and/or 110 V, so that either the cradle comprises a connector straight to the mains or the cradle comprises a port for a connection to a computer. The port can be any kind of suitable port, such as a micro USB port, but the skilled person will understand that any other kinds of ports can be used for connection.

As described above, the portable device and/or the cradle can comprise a visible and/or audible indicator in connection with the power management means to indicate several issues, such as charge level of the power means, charging status, etc.

Furthermore, in an embodiment, the control means further comprises location tracking means 216. In one embodiment, the GSM module is also used for location tracking. In another either additional or alternative embodiment, the location tracking means comprises a GPS module, which is used for tracking of the motion detection means. It is obvious to the skilled person that another tracking means can also use to obtain location information.

The arrangement further comprises an external entity as described above. The external entity can comprise e.g. a database for data monitored by monitoring means of the present invention and software for processing the data transferred from the portable device. In one embodiment, the software in the external entity is arranged to calculate the correlation between activity data and heart rate data for each user and to provide user's heart rate profile based on his/hers activity data.

Preferably, the external entity further comprises an application for a user to monitor his/hers workout progress, physical fitness and/or heart rate profile as well as other information, which can be provided based on data obtained by monitoring means in the portable device during an exercise, for example. The application can be downloadable to a user's computer and/or available over communication network(s).

As described above, data transfer between heart rate monitoring means and control means can be arranged in several ways. In addition, data transfer from the portable device 102 to an external entity, such as a cloud 106 or a server, can be arranged in several ways. In one embodiment, the data transfer means in the control means comprises means for transferring data to the external entity via wireless cellular communications system. Such means can comprise e.g. at least one transceiver and a GSM module. Advantageously, the data transfer is arranged to be between the portable device 102 and the external entity, which external entity is accessible via one or more wireless and/or wired network(s). For communication purposes via GSM Radio network, the GSM module comprises an internal SIM card or other means for enabling the communication, and a unique communication ID for the communication. In other words, data from the portable device is transferred straight to the external entity via wireless cellular communications system by using the transferring means of the portable device.

In another additional or alternative embodiment, the control means further comprises physical means, such as a USB port, for data transfer between the portable device and the external entity. In the present embodiment, the data can be first transferred to a terminal device, e.g. a personal computer, a smart phone, a tablet to name a few, and depending on embodiment, processed and performed on that device or transferred further to the external entity, for example a cloud. Yet, in another additional or alternative embodiment, the control means further comprises RF means, such as BLUETOOTH for data transfer between the portable device and the external entity. The skilled person will understand that the preceding embodiments are meant for examples of data transfer, not for limiting the invention.

Data transferred from the portable device to the external entity may comprise heart rate data, if monitored, activity data and location information in embodiments comprising location tracking means. The control means may be configured to transfer also other information, such as device configuration data and device status information. Data transferred from the external entity to the portable device may contain e.g. software updates etc. Some known methods for compressing data before transmission can be used, which is obvious for the skilled person.

In an embodiment, data transfer is continuously performed, when the portable device is activated and/or heart rate and/or activity is/are monitored by the portable device. In one embodiment, the controlling means further comprises a buffer, for example, having a memory, wherein the data is stored and from where the data is further transferred. Also in this embodiment, the data transfer can be continuous, i.e. the data is transferred via the buffer and the buffer is ensuring that any interruption in data transfer does not cause data loss. In embodiments having a continuous data transfer, transferring is preferably continued as long as the portable device is in its activated state and/or heart rate and/or activity is/are monitored by the portable device. It is advantageous to arrange the data transfer so that all monitored data will be transferred to the external entity.

In an embodiment, the monitored heart rate and/or activity data is stored in a memory, and data is transferred from the memory to the external entity. In one embodiment, data transfer is performed after a predetermined time period has elapsed. Measuring of time is preferably started same time with beginning of monitoring and the predetermined time period can be selected according to the size of the memory/memories of the controlling means. The predetermined time period can be e.g. 10-15 minutes.

In one embodiment, the controlling means are arranged to monitor free space of the memory and to start the data transfer, when a predetermined limit is reached. In one embodiment, the user is informed of the necessity to transfer data, before starting the data transfer so that the user has a possibility to postpone the transfer.

In one embodiment, the data transfer is started when the portable device is placed to the cradle for charging. In this embodiment, the portable device, e.g. controlling means in the device, can be indicated about start of the charging so that it can start the data transfer at the same time. In one embodiment, the same means used for securing the portable device to the cradle are used for indicating the portable device about charging.

In an embodiment, heart rate monitoring is paused, if in process, for the duration of the data transfer. Heart rate monitoring can be disturbed by the data transfer, so it can be advantageous to pause the heart rate monitoring, when data transfer is started. In a preferable embodiment, a heart rate profile is generated from the monitored activity data for the duration of paused monitoring. The utilization of the personal correlation between activity data and heart rate data requires an accomplished learning phase.

Figure 3:
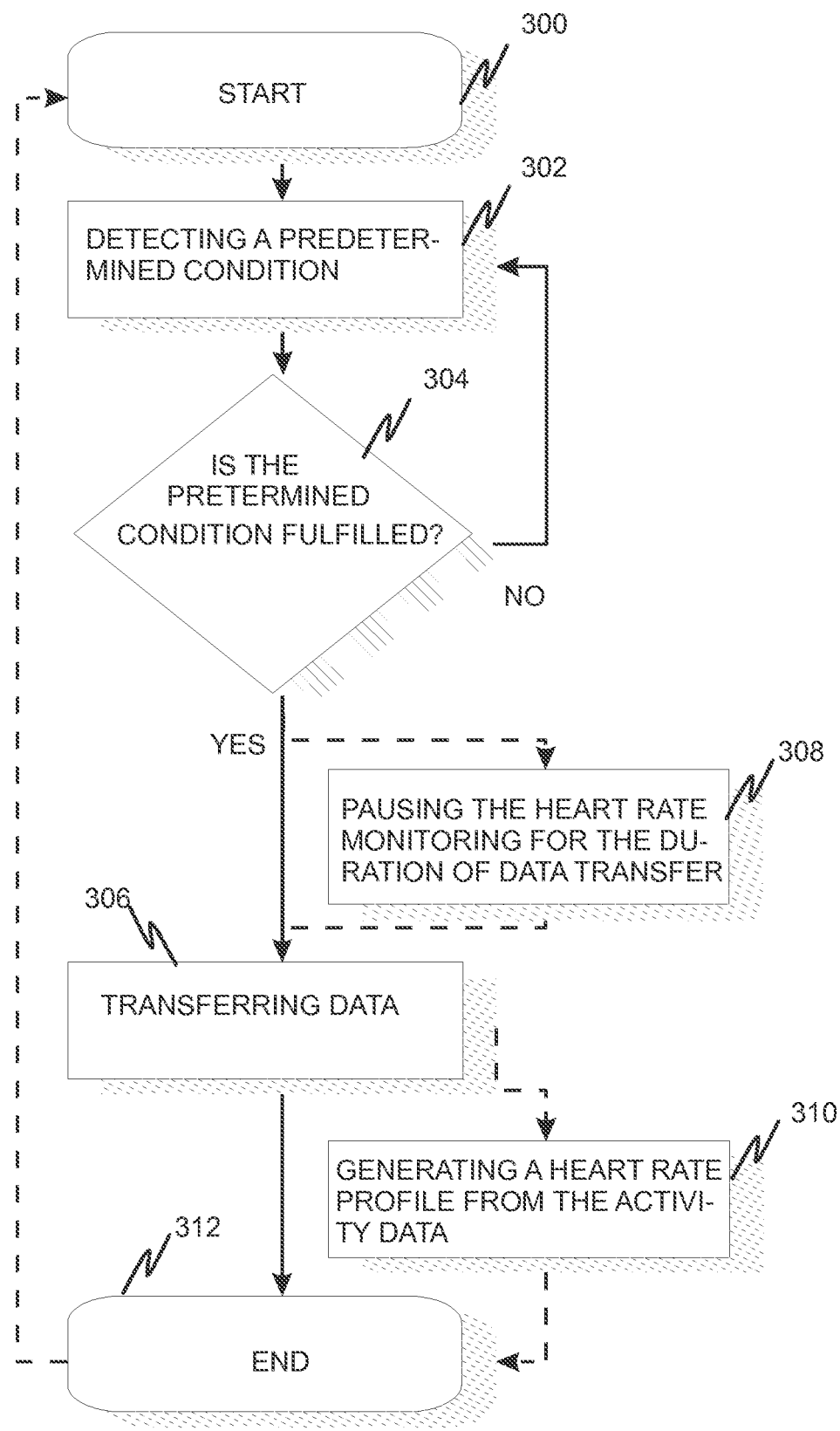
FIG. 3 is a flow chart disclosing an embodiment of a method in accordance of the present invention.

FIG. 3 is a flow chart disclosing an embodiment of a method in accordance of the present invention. At step 300, the method of data transfer between the heart rate and activity monitor arrangement according to the present invention and an external entity is started. Typically, the method is started, when the portable device is activated and/or data monitoring is started.

At step 302, the arrangement of the present invention is arranged to detect a predetermined condition. The predetermined condition is detected by e.g. controlling means of the portable device in order to start the data transfer. As described above, the predetermined condition can be, depending on embodiment, activating the portable device, starting of the heart rate and/or activation monitoring, elapsed time period since activating the device and/or starting the monitoring, space of free memory, charging the device. The skilled person will understand that the above mentioned examples of embodiments do not limit the invention, but other predetermined conditions can also be used.

At step 304, the arrangement decides if the predetermined condition is fulfilled. If it is not, the method returns to step 302 to detect the predetermined condition. If the predetermined condition is fulfilled, the method continues to step 306 and the data transfer is started. In one embodiment, the data transfer continuers as long as the portable device and/or the external entity provide data to be transferred. In another embodiment, certain amount of data is transferred at a time or data transfer goes on for certain amount of time.

In an embodiment, the method continues to step 308 (presented with dotted line in FIG. 3) and the heart rate monitoring is paused for the duration of the data transfer before the transfer is started. After step 308, the method continues to the step 306 of data transfer.

In another embodiment, the method continues to step 310 (presented with dotted line in FIG. 3) after transferring data at step 306. At step 310, a heart rate profile for the user is generated from the activity data for the duration of paused heart rate monitoring.

The method of the data transfer is stopped at step 312. As denoted by dotted line, the method of data transfer can be started all over again from step 300. Depending on embodiment, the method can be repeated endlessly or in certain time intervals.

The scope of the invention is determined by the attached claims together with the equivalents thereof. The skilled persons will again appreciate the fact that the explicitly disclosed embodiments were constructed for illustrative purposes only, and the scope will cover further embodiments, embodiment combinations and equivalents that better suit each particular use case of the invention.

The invention claimed is:

1. A heart rate and activity monitor device comprising:
   a heart rate monitor comprising a chest strap and electrodes configured to monitor a user's heart rate;
   a motion detector comprising a 3D accelerometer or a gyroscope configured to monitor said user's activity;
   one or more processors configured to obtain control data from said heart rate monitor and/or from said motion detector and configured to pause heart rate monitoring; and
   a wireless cellular communications system comprising at least one transceiver configured to send and receive data, the wireless cellular communications system being configured to transfer heart rate and activity data monitored by said heart rate and activity monitor device to an external entity, when charging the heart rate and activity monitor device is started,
   wherein the one or more processors pauses the heart rate monitoring when data transfer is started.

2. The heart rate and activity monitor device according to claim 1, wherein said wireless cellular communications system comprises a 2G cellular communications module.

3. The heart rate and activity monitor device according to claim 1, wherein said monitored data is stored by a memory before data transfer.

4. The heart rate and activity monitor device according to claim 3, wherein the data is transferred after a predetermined time period has elapsed.

5. The heart rate and activity monitor device according to claim 1, wherein said heart rate monitoring is paused, when in process, for the duration of data transfer.

6. The heart rate and activity monitor device according to claim 5, wherein a heart rate profile is generated from said activity data for the duration of paused monitoring.

7. The heart rate and activity monitor device according to claim 1, wherein at least the motion detector and the processor are provided in a portable device.

8. The heart rate and activity monitor device according to claim 1, wherein the external entity is a cloud system or a server.

9. The heart rate and activity monitor device according to claim 1, wherein the data is transferred directly from the heart rate and activity monitor device to the external entity by the wireless cellular communications system.

10. The heart rate and activity monitor device according to claim 1, wherein the one or more processors receives an indication that the charging has started, and
   the wireless communications system is configured to transfer the heart rate and activity data monitored by the heart rate and activity monitor device to the external entity, when the one or more processors receives the indication of the start of the charging.

11. A method for transferring data between the heart rate and activity monitor device according to claim 1 and the external entity, the method comprising: detecting a predetermined condition; and transferring the data when said predetermined condition is fulfilled.

12. The method for transferring data according to claim 11, further comprising pausing said heart rate monitoring, when in process, for the duration of data transfer.

13. The method for transferring data according to claim 12, further comprising generating a heart rate profile from said activity data for the duration of paused heart rate monitoring.

* * * * *